US010485473B2

(12) United States Patent
Bonifas et al.

(10) Patent No.: US 10,485,473 B2
(45) Date of Patent: Nov. 26, 2019

(54) PORTABLE HYDRATION SENSOR

(71) Applicant: 3M INNOVATIVE PROPERTIES COMPANY, St. Paul, MN (US)

(72) Inventors: Andrew P. Bonifas, Alberta (CA); Ronald D. Jesme, Plymouth, MN (US); Nicholas T. Gabriel, Woodbury, MN (US); Andrew J. Ouderkirk, Kirkland, WA (US); Erin A. McDowell, Afton, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/098,919

(22) PCT Filed: May 1, 2017

(86) PCT No.: PCT/US2017/030356
§ 371 (c)(1),
(2) Date: Nov. 5, 2018

(87) PCT Pub. No.: WO2017/192429
PCT Pub. Date: Nov. 9, 2017

(65) Prior Publication Data
US 2019/0142332 A1 May 16, 2019

Related U.S. Application Data

(60) Provisional application No. 62/332,886, filed on May 6, 2016.

(51) Int. Cl.
*A61B 5/00* (2006.01)
*A61B 5/01* (2006.01)

(52) U.S. Cl.
CPC ............... *A61B 5/441* (2013.01); *A61B 5/01* (2013.01); *A61B 5/4875* (2013.01)

(58) Field of Classification Search
CPC .......... A61B 5/441; A61B 5/01; A61B 5/4875
(Continued)

(56) References Cited

U.S. PATENT DOCUMENTS

| 2008/0275319 A1* | 11/2008 | Van Gogh | A61B 5/0095 600/316 |
| 2011/0213559 A1* | 9/2011 | Pollack | A61B 5/0008 702/19 |

(Continued)

FOREIGN PATENT DOCUMENTS

| WO | WO 2007-079008 | 7/2007 |
| WO | WO 2008-024860 | 2/2008 |

(Continued)

OTHER PUBLICATIONS

"Partnering to help build the future of wearable technology", [retrieved from the internet on Dec. 19, 2018], URL <https://www.logicpd.com/success_stories/partnering-build-wearable-technology/>, 2 pages.

(Continued)

*Primary Examiner* — Daniel L Cerioni
(74) *Attorney, Agent, or Firm* — X. Christina Huang

(57) ABSTRACT

A portable sensor for measuring a hydration level of an object in close physical proximity with the sensor includes a portable housing having a total volume of less than about 50 cm3. First circuitry disposed in the housing includes a thermal source, a controller electrically coupled to the thermal source, a temperature sensing element, and a processor coupled to the temperature sensing element. When the object is in close physical proximity with the sensor, the thermal source is energized by the controller with a signal having a known function of time. The object affects a time variation of a temperature of the thermal source, the temperature sensing element senses the affected time variation of the temperature of the thermal source, and the processor (Continued)

determines a hydration level of the object based on a characteristic of the affected time variation of the temperature of the thermal source.

14 Claims, 4 Drawing Sheets

(58) Field of Classification Search
USPC .......................................................... 600/549
See application file for complete search history.

(56) References Cited

U.S. PATENT DOCUMENTS

| 2013/0245388 | A1* | 9/2013 | Rafferty | A61B 5/112 |
| | | | | 600/301 |
| 2014/0249388 | A1 | 9/2014 | Howell | |
| 2017/0347891 | A1* | 12/2017 | Rogers | A61B 5/0531 |

FOREIGN PATENT DOCUMENTS

| WO | WO 2012-044871 | 4/2012 |
| WO | WO 2013-149181 | 3/2013 |
| WO | WO 2016-025438 | 2/2016 |
| WO | WO 2016-054348 | 4/2016 |
| WO | WO 2016-073408 | 5/2016 |

OTHER PUBLICATIONS

Dittmar, "Skin Thermal Conductivity: A reliable index of skin blood flow and skin hydration", Clinical Dermatology, 1989, pp. 323-358.
Tsai, "Investigation of Variability of Skin Tissue Intrinsic Thermal Conductivity Measurements", Master of Science Thesis, May 1995, pp. 1-77.
Webb, "Ultrathin Conformal Devices for Precise and Continuous Thermal Characterization of Human Skin," Nature Materials, Sep. 2013, vol. 12, pp. 938-944.
International Search Report for PCT International Application No. PCT/US2017/030356, dated Jul. 4, 2017, 4 pages.

* cited by examiner

PORTABLE HYDRATION SENSOR

CROSS REFERENCE TO RELATED APPLICATIONS

This application is a national stage filing under 35 U.S.C. 371 of PCT/US2017/030356, filed May 1, 2017, which claims the benefit of U.S. application Ser. No. 62/332,886, filed May 6, 2016, the disclosure of which is incorporated by reference in its/their entirety herein.

BACKGROUND

Normal hydration can be important for health and well-being. Even small losses of body water can have a negative effect on muscle strength, endurance and maximal oxygen uptake, so it can be important to quickly, accurately, and continuously measure the hydration level of a human or animal host.

For example, hydration may be measured in a laboratory to test the effects of sports drinks, diets or exercise sessions, in a clinical environment to ensure the wellbeing of patients, by the military to evaluate whether personnel can fulfill active duties while remaining healthy, at major sporting events to ensure that athletes achieve their performance potential, or in a home setting to monitor if a family member, particularly an elderly person or child, is drinking a sufficient amount of fluid.

Hydration can be measured by, for example, acute changes in body mass, blood tests to evaluate hemoglobin concentration, sodium concentration or osmolarity, urine tests, or saliva flow rate, osmolarity or composition.

The practicalities of monitoring hydration levels to promote health and wellbeing are difficult due to the dynamic state of hydration and differences in how individuals respond to fluid gains and losses.

SUMMARY

Current methods for measuring hydration are conducted in a laboratory with expensive equipment. The present disclosure provides an inexpensive sensor for measuring hydration outside the laboratory setting. The hydration sensor is sufficiently small to be portable, and as such can be incorporated into a wide variety of wearable devices, clothing, medical equipment, and the like.

In general, the present disclosure is directed to a portable hydration sensor which, when positioned in close physical proximity to an object, can measure a hydration level of the object. The hydration sensor determines the thermal properties of the object, and these thermal properties are used to infer the hydration state of the object.

In one non-limiting example, where the object is a skin layer of a host, the portable hydration sensor is sufficiently small and compact to integrate into a torso-mounted, head-mounted, or an appendage-mountable wearable device such as a wristwatch, a fitness monitor, or a medical patient monitor. In other embodiments, the portable hydration sensor may be made a part of a wearable item that contacts the skin of the host such as, for example, clothing, eyewear, personal protection equipment, or bandages.

In some embodiments, an interface between the host and sensor can optionally include an interface material. In some embodiments, the interface material can be a disposable or reusable moisture management layer, and the portable hydration sensor can determine a hydration level of the object based on the thermal characteristics of the moisture management layer. In some embodiments, the interface material can more effectively isolate the skin of the host from the thermal source of the sensor, which can improve sensor response times.

In one aspect, the present disclosure is directed to a portable sensor for measuring a hydration level of an object in close physical proximity with the portable sensor. The sensor includes a portable housing having a total volume of than about 50 $cm^3$; and a first circuitry disposed in the housing. The first circuitry includes a thermal source, a controller electrically coupled to the thermal source, a temperature sensing element, and a processor coupled to the temperature sensing element. When an object is in close physical proximity with the thermal source and the temperature sensing element, the thermal source is energized by the controller with a signal having a known function of time, the object affects a time variation of a temperature of the thermal source, the temperature sensing element senses the affected time variation of the temperature of the thermal source, and the processor determines a hydration level of the object based on a characteristic of the affected time variation of the temperature of the thermal source.

In another embodiment, the present disclosure is directed to a portable sensor for measuring a thermal characteristic of an object in close physical proximity with the portable sensor, including a portable housing and one or more circuitries disposed in the housing. Each circuitry includes a thermal source; a controller electrically coupled to the thermal source, and a temperature sensing element. A moisture management layer is in thermal contact with the thermal source and the temperature sensing element. The moisture management layer, when substantially dry, has a known time variation of temperature in response to the thermal source being energized with a signal having a known function of time. When an object is in close physical proximity with the moisture management layer, the moisture management layer controls a rate of moisture transfer between the object and the moisture management layer, the thermal source is energized by the controller with the signal having the known function of time, the energized thermal source delivers thermal energy to the moisture management layer, and the temperature sensing element senses a time variation of a temperature of the moisture management layer.

In another embodiment, the present disclosure is directed a method of sensing a fluid content of an object, including steps of: transferring fluid from an object to a moisture management layer placed in close physical proximity to the object, the moisture management layer, when substantially dry, having a known time variation of temperature in response to thermal energy having a known function of time delivered to the moisture management layer; delivering to the moisture management layer thermal energy having the known function of time; and sensing a time variation of a temperature of the moisture management layer.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

Figure 1:
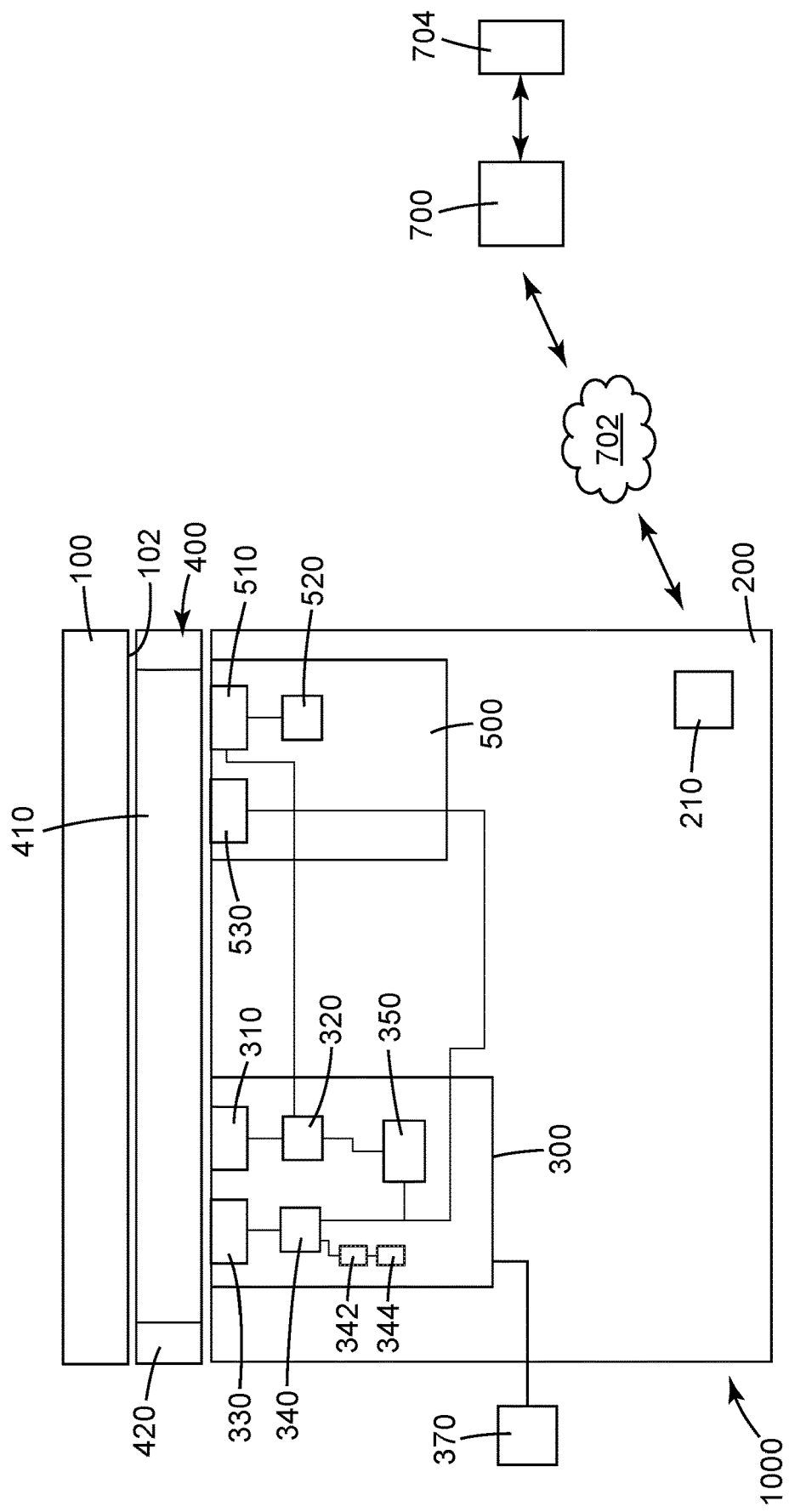
FIG. 1 is a schematic, cross-sectional diagram of an embodiment of a portable temperature sensor.

Referring to FIG. 1, a portable sensor 1000 measures a hydration level of an object 100 in close physical proximity with the portable sensor. The portable sensor 1000 includes a housing 200 which, in various example embodiments that are not intended to be limiting, can have a total volume of less than about 100 cm$^3$, or less than about 50 cm$^3$, or less than about 20 cm$^3$, less than about 10 cm$^3$, less than about 5 cm$^3$, or less than about 1 cm$^3$.

The portable sensor 1000 includes a first electrical circuitry 300 disposed in the housing 200. The first circuit 300 includes a thermal source or heater 310 maintained in close thermal contact with the object 100 and substantially thermally isolated from the housing 200. The thermal source 310 locally warms or cools at least a portion of a surface 102 of the object 100. The thermal source 310 may vary widely depending on the intended application, and may include any heater circuit such as, for example, a resistance heater, an induction heater, and the like. In some embodiments, the thermal source may be powered by a power source 350 as described in more detail below. In another embodiment, the thermal source 310 may utilize waste heat of a subsystem to alter the temperature of the object 100. For example, when a Bluetooth radio is turned on, its waste heat could be used as the thermal source 310, and hydration sensing of the object 100 could be opportunistically determined at these times with little additional power expenditure.

The first circuit 300 further includes a controller 320 electrically coupled to the thermal source 310. The controller 320 provides a constant (or a known power vs. time) input power to the thermal source 310.

A temperature sensing element 330, which in various embodiments can be adjacent to or spaced apart from the thermal source 310, is electrically coupled to the thermal source 310. The temperature sensing element 330 is electrically coupled to a processor 340, which is used to evaluate the results of the temperature sensing element 330 over time and, based at least in part on these results, infer hydration of the object 100.

For example, the processor 340 executes instructions stored in memory 342 or instructions stored on storage devices 344. Memory 342 or storage devices 344 may store sensor information including calibration data, reference information, serial number, model, usage history, or construction information. Memory 342, which may be a non-transient, computer-readable storage medium, is configured to store information, and in some embodiments may include a temporary memory, i.e. an area for information to be maintained when the first circuit 300 is turned off. Examples of such temporary memory include volatile memories such as random access memories (RAM), dynamic random access memories (DRAM), and static random access memories (SRAM). The memory 342 also maintains program instructions for execution by the processor 340. In some embodiments, the processor and controller may be combined into one element.

The storage devices 344 also include one or more non-transient computer-readable storage media. The storage devices 344 are generally configured to store larger amounts of information than memory 342, and may further be configured for long-term storage of information. In some examples, storage devices 344 include non-volatile storage elements such as, for example, magnetic hard discs, optical discs, floppy discs, flash memories, ferroelectric random access memories (FRAM), or forms of electrically programmable memories (EPROM) or electrically erasable and programmable (EEPROM) memories.

In some embodiments, a temperature-dependent electrically resistive element 360 disposed in the housing 200 can function as both the thermal source 310 and the temperature sensing element 330.

In the embodiment shown in FIG. 1, the first circuit 300 includes an internal power source 350 disposed in the housing 200, although power sources 370 external to the housing 200 may be used in addition to or in place of the internal power source 350. The power source 350 is electrically coupled to at least one of the thermal source 310, the controller 320, the temperature sensing element 330, and the processor 340. In various embodiments, the power source 350 includes one or more of a battery, a fuel cell, a capacitor, a supercapacitor, and a mechanical potential energy storage source. Non-limiting examples of power sources 350 include single-use power sources, rechargeable power sources, and/or power sources developed from nickel-cadmium, lithium-ion, or other suitable material. In some embodiments, the mechanical potential energy storage source for the power source 350 can include one or more springs, compressed fluid, an elevated weight, and a flywheel.

In some embodiments, the portable sensor 1000, or the device of which the portable sensor 1000 is a part, such as, for example, a smart phone, a personal digital assistant (PDA), a tablet computer, a wearable computer or watch, a laptop computer, a video-game console, or the like, is equipped with communication elements 210. The communication elements 210 enable the sensor 1000 to establish communicative connections when they are brought into proximity of other devices capable of establishing a communicative connection. For example, the communicative connection may be established through a near field communications (NFC) protocol, Bluetooth, ANT, ZigBee, WiFi, or through a variety of other protocols.

In some embodiments, the portable sensor 1000 may be connected to a server 700 (or cloud-based platform) through a data network 702. The server 700 is additionally connected to a database 704. The network 702 may be either a wired or a wireless network, and may include elements of a Bluetooth network, WiFi network, cellular network, a voice over internet protocol (VoIP) network, a public switched telephone network (PSTN), or a combination thereof. Example networks include but are not limited to a long term evolution (LTE) network, a global system for mobile communications (GSM) network, a code division multiple access (CDMA) network, a fiber optic network, and other voice or data networks. The network 702 may also include elements of wireless local area network (WLAN) or wireless personal area network (WPAN) networks that enable the sensor 1000 to connect to other components of the network, for example an LTE network, a WiFi network, or a Bluetooth network.

The network 702 allows the sensor 1000 to communicate with the server 700. For example, the sensor 1000 may transmit information to the server 700 and receive information from the server 700. The server 700 includes processors and memory configured to receive information from the sensor 1000 and to provide information to the sensor 1000. The information received by the server 700 may include data pertaining to a user account affiliated with the sensor 1000, data pertaining to contextual information relevant to the sensor 1000 or a user account affiliated with the client device, and the like.

The database 704 may store a variety of information, including, e.g., information pertaining to one or more user accounts for the sensor 1000. Information pertaining to the one or more user accounts may include, but is not limited to, a user account name, the name of a user to whom the user account belongs, verification information for the user account, a social network profile associated with the user account, images associated with the user account, documents and media content associated with the user account, various user account settings, and sensor information including calibration data, reference information, serial number, model, usage history, or construction information.

In operation, the thermal source 310 is energized by the controller 320 with a signal having a known function of time. The thermal source 310 locally warms (or cools) the temperature of at least a portion of the surface 102 of the object 100 in close physical proximity with the thermal source 310. The temperature sensor 330 measures the local temperature change of the surface 102. The object 100 alters or otherwise affects a time variation of a temperature of the thermal source 310. The temperature sensing element 330 senses the affected time variation of the temperature of the thermal source 310, and the processor 340 determines a hydration level of the object 100 based on a characteristic of the affected time variation of the temperature of the thermal source 310.

In various example embodiments, which are not intended to be limiting, the characteristic of the affected time variation utilized by the processor 340 to determine hydration level of the object 100 includes a time rate of change of the affected time variation of the temperature of the thermal source 310, or a magnitude of the temperature when a time rate of change of the affected time variation of the temperature of the thermal source 310 is less than a threshold value.

In various embodiments, the processor 340 may be configured to provide a wide variety of output signals. For example, the processor 340 may produce a digital output energizing a LED or number of LEDs, a digital display, or digital data communicated to another device via a data download cable or wirelessly. In some embodiments, the output of the processor 340 may be analog, such as controlling the brightness of a LED, or the apparent color of a LED, or a combination thereof.

Figure 2:
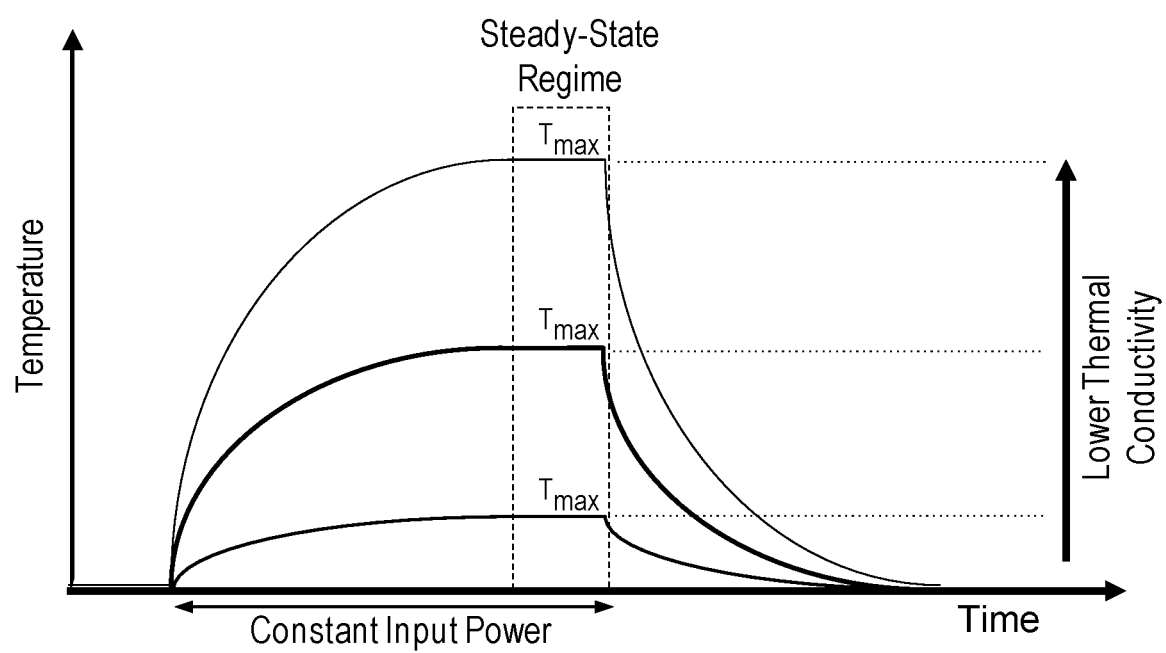
FIG. 2 is a schematic profile of a heater element before, during, and after constant input power, wherein the heater element in thermal contact with 3 different materials each having different thermal properties.

For example, if a constant input power is applied by the controller 320 to the thermal source 310, as shown in FIG. 2, the increase in temperature of the thermal source 310 in proximity with the surface 102 of the object 100 will have an associated time constant and an associated steady state temperature. This increase in temperature of the thermal source 310 will have a temperature-time profile dependent on the material of the surface 102 of the object 100 proximal the thermal source 310.

In one example, which is not intended to be limiting, the thermal source 310 can be placed in close proximity to an area of human skin to measure the hydration level thereof. The hydration level of the skin near the thermal source 310 may be inferred from the thermal properties of the skin, which indicate its hydration status. For example, when the surface of the skin proximal the thermal source 310 is relatively dehydrated, its thermal conductivity is relatively low, conversely, when the surface of the skin is relatively hydrated its thermal conductivity is relatively high. If the skin surface is relatively well hydrated, the temperature rise before reaching steady-state will be relatively small, as opposed to a relatively large temperature rise when the skin surface is relatively dry.

As noted above, the surface 102 of the object 100 should be maintained in close physical proximity with the thermal source 310 and the temperature sensing element 330. In various embodiments, an external force may be applied to maintain the physical proximity of the object 100 and the thermal source 310 and the temperature sensing element 330. In some embodiments, the object 100 and the portable sensor 1000 should be maintained in sufficiently close proximity to one another such that the components of the portable sensor 1000 are in close thermal contact with the surface 102 of the object 100. Close thermal contact means that thermal energy can transfer from the thermal source 310 to the surface 102 of the object 100 to alter the temperature of at least a portion of the surface 102; or, sufficient thermal energy can transfer from the object 100 to the temperature sensing element 330 such that the temperature sensing element 330 can detect a change in the temperature of the surface 102 of the object 100. In various embodiments, thermal energy transfers from the components of the portable sensor 1000 to the surface 102 of the object 100 by at least one of thermal conduction, radiation, or convection. In some embodiments, the thermal energy transfers from the components of the portable sensor 1000 to the surface 102 of the object 100 predominately by conduction, or substantially by conduction.

In one example, which is not intended to be limiting, if the portable sensor 1000 is incorporated into a wrist watch or a fitness monitor, the band of the watch maintains the relative positions of the sensor 1000 and the surface of the skin of the host such that the separation between the sensor 1000 and the skin of the host is no more than 10 mm, or no more than about 5 mm. Larger separations between the sensor 1000 and the surface of the skin of the host may temporarily occur, but if thermal energy cannot effectively transfer from the thermal source 310 to the skin of the host, suspension or cessation of device measurement activity may result. Larger separations between the sensor 1000 and the object 100 may adversely impact the accuracy of the transfer of thermal energy between the object and at least one of the thermal source 310 and the temperature sensing element 330, which can cause erroneous hydration values (or no hydration values) to be output by the sensor 1000.

Figure 3:
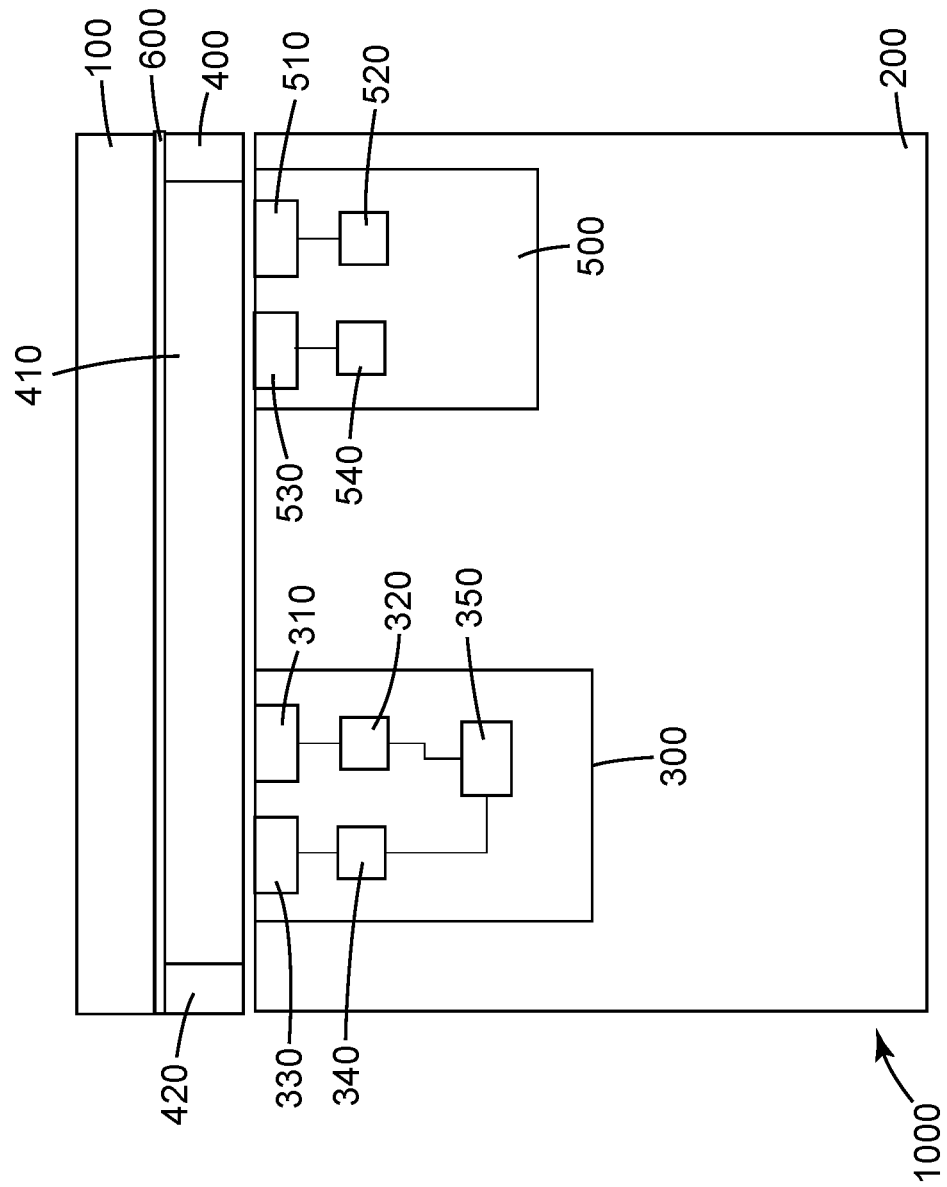
FIG. 3 is a schematic, cross-sectional diagram of another embodiment of a portable temperature sensor

For example, in another embodiment, the object 100 is kept in close physical proximity with the thermal source 310 and the temperature sensing element 330 by an adhesive layer 600 between the surface 102 of the object 100 and the housing 200 (see FIG. 3). The adhesive layer 600 at least temporarily bonds the object 100 to the portable sensor 1000.

As another example, if the portable sensor 1000 is configured to measure a hydration level of human skin in close physical proximity with the portable sensor 1000, the human skin is kept in close physical proximity with the thermal source and the temperature sensing element by an applied external force provided by apparel, a headband, a wristband, a watch, a glove, a soft support brace for wrapping around a human body part, a hard support brace, footwear, and the like.

In another embodiment, the portable hydration sensor 1000 includes a moisture management layer 400 in thermal contact with the thermal source 310 and the temperature sensing element 330. In some embodiments, the moisture management layer 400 is a porous substantially water-repelling or hydrophobic material such as, for example, polytetrafluoroethylene, stretched polytetrafluoroethylene, melamine foam, hydrophobic polyurethanes, hydrophobic silicones, hydrophobic polyacrylates, polyolefins, and polyester. In other embodiments, the moisture management layer 400 is a porous, substantially hydrophilic material such as, for example, hydrophilic polyurethanes, hydrophilic silicones, hydrophilic polyacrylates, hydrogels, cellulose, polyacrylic amides, polyamides, ethoxylated graphed polymers, natural fibers, rayon, and cotton. In some embodiments, the moisture management layer 400 has an adhesive property. In some embodiments, the moisture management layer 400 and the adhesive layer 600 (FIG. 3) are combined.

In some embodiments, the moisture management layer 400 is selected from materials suitable to control a rate of moisture transfer to or from the moisture management layer 400 fro or to the surface 102 of the object 100. In various embodiments, transpiration may be controlled by the use of hydrophilic or hydrophobic moisture control materials for the moisture management layer 400, which may be in the form of a reusable or disposable pad. Suitable materials for controlling the rate of moisture transfer include, but are not limited to, foamed polymeric materials such as polyurethanes, polyolefins, polyesters, polyvinyl chlorides, ethylene vinyl acetate, polyvinyl alcohols, polyvinyl acetates, and or nonwoven materials such as polypropylene, polyethylene terephthalate, cellulose, rayon, synthetic rayon, nylon, polyester, and polyethylene. In some embodiments, the transpiration control by the moisture management layer 400 can be used to augment thermal contact between the object 100 and the hydration sensor 1000.

The moisture management layer 400, when substantially dry, has a known time variation of temperature in response to the thermal source 310 being energized by the controller 320 with a signal having the known function of time. In some embodiments, the moisture management layer 400, when containing a known amount of fluid, has a known time variation of temperature in response to the thermal source 310 being energized by the controller 320 with a signal having the known function of time. When the surface 102 of the object 100 is in close physical proximity with the moisture management layer 400, and the moisture management layer 400 is disposed between the object 100 and the thermal source 310 and the temperature sensing element 330, the moisture management layer 400 controls a moisture transfer rate between the object 100 and the moisture management layer 400. When the thermal source 310 is energized by the controller 320 with the signal having the known function of time, the energized thermal source 310 delivers thermal energy to the moisture management layer 400, the moisture transfer between the surface 102 of the object 100 and the moisture management layer 400 affects a time variation of a temperature of the thermal source 310. The temperature sensing element 330 senses the affected time variation of the temperature of the thermal source 310, and the processor 340 determines a hydration level of the object 100 based on a characteristic of the affected time variation of the temperature of the thermal source 310.

In some embodiments, wherein the moisture management layer 400 is sufficiently thick and/or the temperature sensing element 330 senses the time variation of the temperature of the thermal source 310 over a sufficiently short period of time such that substantially no thermal energy, or no thermal energy, is delivered by the portable sensor 1000 to the surface 102 of the object 100 while the temperature sensing element 330 senses the time variation of the temperature of the thermal source 310.

In some embodiments, a suitable thickness of the moisture management layer 400 necessary to prevent delivery of thermal energy from the portable sensor 1000 to the object 100 as the sensing element 330 senses the time variation of the temperature of the thermal source 310 is about 0.1 mm to about 10 mm, or about 0.5 mm to about 3 mm. In various embodiments, the sensing element 330 senses the time variation of the temperature of the thermal source 310 over a time period of about 0.1 second to about 10 minutes, or about 1 seconds to about 60 seconds.

In some embodiments, the moisture management layer 400 includes an inner region 410 surrounded by a perimeter region 420. The inner region 410 is substantially hydrophilic (water-absorbing) and the perimeter region 420 is substantially hydrophobic (water-repelling).

Referring again to FIG. 1, in some embodiments the portable sensor 1000 further includes reference circuitry 500 that provides a reference signal to be used by a processor in assessing the hydration level of the object 100. The reference circuitry includes a second thermal source 510, a second controller 520 electrically coupled to the second thermal source 510, and a second temperature sensing element 530.

In some embodiments, the object 100 is in close physical proximity with the thermal source 310 and the temperature sensing element 330 of the first circuitry 300, but the object 100 is not in close physical proximity with the thermal source 510 and the temperature sensing element 530 of the reference circuitry 500, so the reference circuitry 500 is thermally isolated from the first circuitry 300. However, such a thermal isolation arrangement between the first circuitry 300 and the reference circuitry 500 is not required, and either or both of the thermal sources 310,510 and the temperature sensing elements 330,530 may be in close physical proximity with object 100.

In operation, the thermal sources 310, 510 are energized by the controllers 320, 520 with a signal having a known function of time. The object 100 affects a time variation of a temperature of at least one of the thermal sources 310, 510, and at least one of the temperature sensing elements 330, 530 sense the affected time variation of the temperature of the affected thermal source 310, 510. The processor 340 then compares the affected time variation of the temperatures of the thermal sources 310, 510 of the first and reference circuitries 300, 500, and determines the hydration level based on a characteristic of the affected time variation of the temperature of at least one of the thermal sources 310, 510.

In some embodiments, for example, the object 100 has substantially no effect on the time variation of a temperature of the thermal source 510 of the reference circuitry 500, and the reference circuitry 500 provides a reference signal to be used by the processor 340 in the determination of the hydration level of the object 100.

In other embodiments, the controller 520 applies to the reference thermal source 510 a signal having a known function of time, and the temperature sensing element 530 of the reference circuitry 500 senses a time variation of the temperature of the thermal source 510. The time variation of the temperature of the thermal source 510 may also be used by the processor 340 to determine the hydration level of the object 100 (alone or including the sensed time variation information from the thermal source 310 and the sending element 330).

As shown in FIG. 1, the thermal sources 310, 510 can be energized by the same signal from the controller 320. In the alternative, as shown in FIG. 3, the thermal sources 310, 510 can be energized by signals from a first controller 320 in the first circuit 300 and a second controller 520 in the reference circuit 500.

The portable hydration sensor 1000 shown in FIGS. 1 and 3 can be used to sense hydration of a wide variety of hosts in which moisture level may impact product quality such as, for example foods, construction materials (wood, areas susceptible to mold), pharmaceuticals, soil and the like. In these examples, the housing 200 may be permanently attached to the object to be measured, or the host may be touched by at least a portion of the sensing system.

Figure 4:
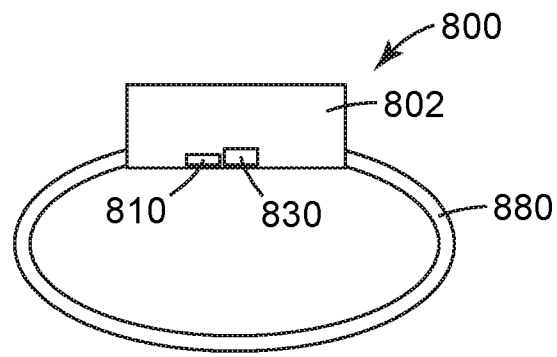
FIG. 4 is a schematic perspective view of a wristwatch including a portable temperature sensor.

The portable hydration sensor 1000 can be used a wide variety of torso-mountable, head-mountable, or appendage-mountable wearable devices such as a wristwatch, a fitness monitor, personal protective apparel, personal protective equipment, or a medical patient monitor. For example, as shown in FIG. 4, a wrist-mounted watch 800 includes a case 802 with a thermal source 810 and a temperature sensor 830. A watch band 880 provides a normal force between the thermal source 810 and temperature sensor 830 and a wearer's skin.

Figure 5:
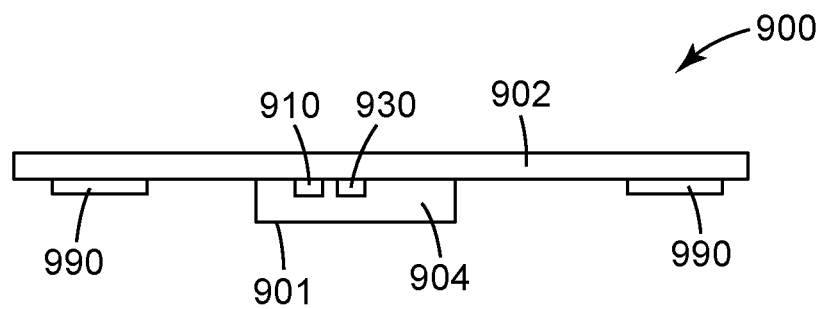
FIG. 5 is a schematic cross-sectional view of a bandage including a portable temperature sensor.

In other embodiments, the portable hydration sensor may be made a part of a wearable item that maintains contact between the thermal source 310 and the sensing element 330 and the skin of the host. Examples include, but are not limited to, clothing such as sports compression clothing, wraps, headbands, undergarments, gloves, footwear, diapers. Additional examples include protective articles such as eyewear, earmuffs, helmets, personal athletic protection equipment such as helmets or mouthpieces, or bandages. For example, as shown in FIG. 5, a bandage 900 includes a nonwoven backing 902 and an absorbent moisture management layer 904. A thermal source 910 and a temperature sensor 930 reside above or within the moisture management layer 904. An adhesive 990 or watch band 880 provides a normal force between the thermal source 910 and temperature sensor 930 and a wearer's skin, which is adjacent to a surface 901 of the moisture management layer 904.

In any of the above embodiments, an interface between the host and sensor can optionally include an interface material such as a disposable or reusable foamed or nonwoven moisture management layer, and the portable hydration sensor can determine a hydration level of the object based on the thermal characteristics of the moisture management layer as described above.

Referring again to FIGS. 1 and 3, in another aspect the present disclosure is directed to a method of sensing a fluid content of an object 100. The method includes transferring fluid from a surface 102 of an object 100 to a moisture management layer 400 placed in close physical proximity to the object. The moisture management layer, when substantially dry, has a known time variation of temperature in response to thermal energy having a known function of time delivered to the moisture management layer 400.

Thermal energy having a known function of time is then delivered to the moisture management layer, and sensing a time variation of a temperature of the moisture management layer is sensed by a sensor including a thermal source 310 and a sensing element 330. In some embodiments, a hydration level of the object is determined based on comparing the sensed time variation of the temperature of the moisture management layer 400 with the known time variation of temperature.

Exemplary Embodiments

Item 1. A portable sensor for measuring a hydration level of an object in close physical proximity with the portable sensor, comprising:
a portable housing having a total volume of less than about 50 cm$^3$; and
a first circuitry disposed in the housing and comprising:
a thermal source;
a controller electrically coupled to the thermal source;
a temperature sensing element; and
a processor coupled to the temperature sensing element, such that when the object is in close physical proximity with the thermal source and the temperature sensing element, the thermal source is energized by the controller with a signal having a known function of time, the object affects a time variation of a temperature of the thermal source, the temperature sensing element senses the affected time variation of the temperature of the thermal source, and the processor determines a hydration level of the object based on a characteristic of the affected time variation of the temperature of the thermal source.

Item 2. The portable sensor of Item 1, wherein the characteristic comprises a time rate of change of the affected time variation of the temperature of the thermal source.

Item 3. The portable sensor of Item 1 or 2, wherein the characteristic comprises a magnitude of the temperature when a time rate of change of the affected time variation of the temperature of the thermal source is less than a threshold value.

Item 4. The portable sensor of any one of Items 1-3 further comprising a power source disposed in the housing and coupled to at least one of the thermal source, the controller, the temperature sensing element, and the processor.

Item 5. The portable sensor of Item 4, wherein the power source comprises one or more of a battery, a fuel cell, a capacitor, a supercapacitor, and a mechanical potential energy storage source.

Item 6. The portable sensor of Item 5, wherein the mechanical potential energy storage source comprises one or more springs.

Item 7. The portable sensor of any one of Items 1-6 further comprising an electrically resistive element disposed in the housing and functioning as the thermal source and the temperature sensing element.

Item 8. The portable sensor of any one of Items 1-7 further comprising a moisture management layer in thermal contact with the thermal source and the temperature sensing element, the moisture management layer, when substantially dry, having a known time variation of temperature in response to the thermal source being energized with the signal having the known function of time, such that when an object is in close physical proximity with the moisture management layer with the moisture management layer disposed between the object and the thermal source and the temperature sensing element, the moisture management layer controls a moisture transfer rate between the object and the moisture management layer, the thermal source is energized by the controller with the signal having the known function of time, the energized thermal source delivers thermal energy to the moisture management layer, the moisture transfer between the object and the moisture management layer affects a time variation of a temperature of the moisture management layer, the temperature sensing element senses the affected time variation of the temperature of the moisture management layer, and the processor determines a hydration level of the object based on a characteristic of the affected time variation of the temperature of the moisture management layer.

Item 9. The portable sensor of Item 8, wherein the moisture management layer comprises an inner region surrounded by a perimeter region, the inner region being substantially water-absorbing and the perimeter region being substantially water-repelling.

Item 10. The portable sensor of Item 8, wherein the moisture management layer comprises a porous substantially water-repelling material.

Item 11. The portable sensor of any one of Items 1-10 further comprising a reference circuitry substantially thermally isolated from the first circuitry and comprising:
a thermal source;
a controller electrically coupled to the thermal source; and
a temperature sensing element.

Item 12. The portable sensor of Item 11, wherein when an object is in close physical proximity with the thermal source and the temperature sensing element of each of the first and reference circuitries, for each of the first and reference circuitries: the thermal source is energized by the controller with a signal having a known function of time, the object affects a time variation of a temperature of the thermal source, the temperature sensing element senses the affected time variation of the temperature of the thermal source, and the portable sensor compares the affected time variation of the temperatures of the thermal sources of the first and reference circuitries.

Item 13. The portable sensor of Item 11, wherein when an object is in close physical proximity with the thermal source and the temperature sensing element of the first circuitry, the object does not affect, or affects very little, a time variation of a temperature of the thermal source of the reference circuitry.

Item 14. The portable sensor of Item 13, wherein the thermal source of the reference circuitry is energized by the controller of the reference circuitry with a signal having a known function of time, and the temperature sensing element of the reference circuitry senses a time variation of the temperature of the thermal source of the reference circuitry.

Item 15. The portable sensor of Item 14, wherein the thermal sources of the first and reference circuitries are energized by a same signal.

Item 16. The portable sensor of Item 11, wherein when an object is in close physical proximity with the thermal source and the temperature sensing element of the first circuitry, the object is not in close physical proximity with the thermal source and the temperature sensing element of the reference circuitry.

Item 17. The portable sensor of Item 11, wherein the reference circuitry further comprises a processor distinct from the processor of the first circuitry.

Item 18. The portable sensor of Item 11, wherein the processor of the first circuitry is also a processor for the reference circuitry.

Item 19. The portable sensor of any one of Items 1-18, wherein when an object is in close physical proximity with the thermal source and the temperature sensing element, the object is in thermal contact with the thermal source and the temperature sensing element.

Item 20. The portable sensor of any one of Items 1-19, wherein when an object is in close physical proximity with the thermal source and the temperature sensing element, the object is kept in close physical proximity with the thermal source and the temperature sensing element by virtue of an adhesive layer at least temporarily bonding the object to the portable sensor.

Item 21. The portable sensor of any one of Items 1-20, wherein when an object is in close physical proximity with the thermal source and the temperature sensing element, the object is kept in close physical proximity with the thermal source and the temperature sensing element by virtue of an applied external force.

Item 22. The portable sensor of Item 1 configured to measure a hydration level of a human skin in close physical proximity with the portable sensor.

Item 23. The portable sensor of Item 22, wherein when a human skin is in close physical proximity with the thermal source and the temperature sensing element, the human skin is kept in close physical proximity with the thermal source and the temperature sensing element by virtue of an applied external force.

Item 24. The portable sensor of Item 23, wherein the external force comprises force from an apparel, a headband, a wristband, a glove, a soft support brace for wrapping around a human body part, a hard support brace, or a footwear.

Item 25. An electronic wrist watch comprising the portable sensor of any one of Items 1-24.

Item 26. The portable sensor of any one of Items 1-25, wherein the portable housing has a total volume of less than about 20 cm$^3$.

Item 27. The portable sensor of any one of Items 1-26, wherein the portable housing has a total volume of less than about 10 cm$^3$.

Item 28. The portable sensor of any one of Items 1-27, wherein the portable housing has a total volume of less than about 5 cm$^3$.

Item 29. The portable sensor of any one of Items 1-28, wherein the portable housing has a total volume of less than about 1 cm$^3$.

Item 30. A portable sensor for measuring a thermal characteristic of an object in close physical proximity with the portable sensor, comprising:
a portable housing;
one or more circuitries disposed in the housing, each circuitry comprising:
a thermal source;
a controller electrically coupled to the thermal source; and
a temperature sensing element; and
a moisture management layer in thermal contact with the thermal source and the temperature sensing element, the moisture management layer, when substantially dry, having a known time variation of temperature in response to the thermal source being energized with a signal having a known function of time,
such that when an object is in close physical proximity with the moisture management layer, the moisture management layer controls a rate of moisture transfer between the object and the moisture management layer, the thermal source is energized by the controller with the signal having the known function of time, the energized thermal source delivers thermal energy to the moisture management layer, and the temperature sensing element senses a time variation of a temperature of the moisture management layer.

Item 31. The portable sensor of Item 30, wherein the moisture management layer is sufficiently thick and/or the temperature sensing element senses the time variation of the temperature of the moisture management layer over a sufficiently short period of time that no, or very little, thermal energy is delivered by the portable sensor to the object while the temperature sensing element senses the time variation of the temperature of the moisture management layer.

Item 32. The portable sensor of Item 30 or 31, wherein the moisture management layer further controls a rate of moisture transfer from the moisture management layer to the object.

Item 33. The portable sensor of any one of Items 30-32 further comprising a processor disposed in the portable housing and coupled to the temperature sensing element, the processor configured to determine a hydration level of the moisture management layer based on the time variation of the temperature of the moisture management layer.

Item 34. The portable sensor of any one of Items 30-32 further comprising a processor disposed in the portable housing and coupled to the temperature sensing element, the processor configured to determine a transfer of thermal energy between the moisture management layer and the thermal source based on the time variation of the temperature of the moisture management layer.

Item 35. The portable sensor of any one of Items 30-34, such that when an object is in close physical proximity with the moisture management layer, the portable sensor measures an amount of moisture transferred from the object to the moisture management layer based on the sensed time variation of the temperature of the moisture management layer.

Item 36. The portable sensor of any one of Items 30-35, wherein the amount comprises a total amount transferred from the object to the moisture management layer.

Item 37. The portable sensor of any one of Items 30-36, wherein the object comprises a human skin.

Item 38. A method of sensing a fluid content of an object, comprising steps of:

transferring fluid from an object to a moisture management layer placed in close physical proximity to the object, the moisture management layer, when substantially dry, having a known time variation of temperature in response to thermal energy having a known function of time delivered to the moisture management layer;

delivering to the moisture management layer thermal energy having the known function of time; and sensing a time variation of a temperature of the moisture management layer.

Item 39. The method of Item 38 further comprising a step of determining a hydration level of the object based on comparing the sensed time variation of the temperature of the moisture management layer with the known time variation of temperature.

Various embodiments of the invention have been described. These and other embodiments are within the scope of the following claims.

The invention claimed is:

1. A portable sensor for measuring a hydration level of an object in close physical proximity with the portable sensor, comprising:
   a portable housing having a total volume of less than about 50 cm$^3$; and
   a first circuitry disposed in the housing and comprising:
   a thermal source;
   a controller electrically coupled to the thermal source;
   a temperature sensing element; and
   a processor coupled to the temperature sensing element,
   a moisture management layer in thermal contact with the thermal source and the temperature sensing element, the moisture management layer, when substantially dry, having a known time variation of temperature in response to the thermal source being energized with the signal having a known function of time, such that when the object is in close physical proximity with the moisture management layer with the moisture management layer disposed between the object and the thermal source and the temperature sensing element, the moisture management layer controls a moisture transfer rate between the object and the moisture management layer, the thermal source is energized by the controller with the signal having the known function of time, the energized thermal source delivers thermal energy to the moisture management layer, the moisture transfer between the object and the moisture management layer affects the time variation of the temperature of the moisture management layer, the temperature sensing element senses the affected time variation of the temperature of the moisture management layer, and the processor determines the hydration level of the object based on a characteristic of the affected time variation of the temperature of the moisture management layer.

2. The portable sensor of claim 1, wherein the characteristic comprises a time rate of change of the affected time variation of the temperature of the thermal source.

3. The portable sensor of claim 1, wherein the characteristic comprises a magnitude of the temperature when a time rate of change of the affected time variation of the temperature of the thermal source is less than a threshold value.

4. The portable sensor of claim 1 further comprising a power source disposed in the housing and coupled to at least one of the thermal source, the controller, the temperature sensing element, and the processor.

5. The portable sensor of claim 4, wherein the power source comprises one or more of a battery, a fuel cell, a capacitor, a supercapacitor, and a mechanical potential energy storage source.

6. The portable sensor of claim 1 further comprising an electrically resistive element disposed in the housing and functioning as the thermal source and the temperature sensing element.

7. The portable sensor of claim 1, wherein the moisture management layer comprises an inner region surrounded by a perimeter region, the inner region being substantially water-absorbing and the perimeter region being substantially water-repelling.

8. The portable sensor of claim 1 further comprising a reference circuitry substantially thermally isolated from the first circuitry and comprising:
   a thermal source;
   a controller electrically coupled to the thermal source; and
   a temperature sensing element.

9. The portable sensor of claim 8, wherein when the object is in close physical proximity with the thermal source and the temperature sensing element of each of the first and reference circuitries, for each of the first and reference circuitries: the thermal source is energized by the controller with a signal having the known function of time, the object affects the time variation of the temperature of the thermal source, the temperature sensing element senses the affected time variation of the temperature of the thermal source, and the portable sensor compares the affected time variation of the temperatures of the thermal sources of the first and reference circuitries.

10. A portable sensor for measuring a thermal characteristic of an object in close physical proximity with the portable sensor, comprising:
   a portable housing;
   one or more circuitries disposed in the housing, each circuitry comprising:

a thermal source;

a controller electrically coupled to the thermal source; and a temperature sensing element; and a moisture management layer in thermal contact with the thermal source and the temperature sensing element, the moisture management layer, when substantially dry, having a known time variation of temperature in response to the thermal source being energized with a signal having a known function of time, such that when the object is in close physical proximity with the moisture management layer, the moisture management layer controls a rate of moisture transfer between the object and the moisture management layer, the thermal source is energized by the controller with the signal having the known function of time, the energized thermal source delivers thermal energy to the moisture management layer, and the temperature sensing element senses the time variation of the temperature of the moisture management layer.

11. The portable sensor of claim 10, wherein the moisture management layer is sufficiently thick and/or the temperature sensing element senses the time variation of the temperature of the moisture management layer over a sufficiently short period of time that no, or very little, thermal energy is delivered by the portable sensor to the object while the temperature sensing element senses the time variation of the temperature of the moisture management layer.

12. The portable sensor of claim 10 further comprising a processor disposed in the portable housing and coupled to the temperature sensing element, the processor configured to determine a transfer of thermal energy between the moisture management layer and the thermal source based on the time variation of the temperature of the moisture management layer.

13. The portable sensor of claim 10, such that when the object is in close physical proximity with the moisture management layer, the portable sensor measures an amount of moisture transferred from the object to the moisture management layer based on the sensed time variation of the temperature of the moisture management layer.

14. The portable sensor of claim 10, wherein the amount comprises a total amount transferred from the object to the moisture management layer.

* * * * *